US009759730B2

(12) United States Patent
Rechner

(10) Patent No.: US 9,759,730 B2
(45) Date of Patent: *Sep. 12, 2017

(54) METHOD AND DEVICE FOR THE DETERMINATION OF PLATELET FUNCTION UNDER FLOW CONDITIONS

(71) Applicant: SIEMENS HEALTHCARE DIAGNOSTICS PRODUCTS GMBH, Marburg (DE)

(72) Inventor: Andreas Rechner, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 37 days.

This patent is subject to a terminal disclaimer.

(21) Appl. No.: 14/509,907

(22) Filed: Oct. 8, 2014

(65) Prior Publication Data
US 2015/0093770 A1 Apr. 2, 2015

Related U.S. Application Data

(62) Division of application No. 11/790,853, filed on Apr. 27, 2007, now abandoned.

(30) Foreign Application Priority Data

Apr. 28, 2006 (DE) .................. 10 2006 020 385

(51) Int. Cl.
C12Q 1/56 (2006.01)
G01N 33/86 (2006.01)

(52) U.S. Cl.
CPC ....... G01N 33/86 (2013.01); G01N 2333/726 (2013.01)

(58) Field of Classification Search
CPC ... A61K 8/04; A61K 8/06; A61K 8/19; A61K 8/89; A61K 8/891; A61K 8/92; A61K 2039/505; A61Q 17/04; A61Q 19/00; G01N 2333/726; G01N 33/86
See application file for complete search history.

(56) References Cited

U.S. PATENT DOCUMENTS

| 5,051,239 A | 9/1991 | von der Goltz | |
| 5,622,867 A * | 4/1997 | Livesey .................... | A01N 1/02 424/532 |
| 6,702,987 B1 * | 3/2004 | Kundu ................ | G01N 33/4905 422/421 |
| 2004/0138229 A1 * | 7/2004 | Bryant ................. | C07D 215/48 514/253.06 |
| 2007/0254324 A1 | 11/2007 | Rechner | |

FOREIGN PATENT DOCUMENTS

| EP | 0716744 B1 | 11/2001 | |
| JP | 57-000552 A | 1/1982 | |
| JP | 1-201157 A | 8/1989 | |
| JP | 9-502532 A | 3/1997 | |
| WO | WO 96/00898 A1 | 1/1996 | |
| WO | WO 97/34698 A1 | 9/1997 | |
| WO | WO-02/074322 A2 | 9/2002 | |
| WO | WO 2005/007868 A2 | 1/2005 | |
| WO | WO 2005007868 A2 * | 1/2005 | ............. G01N 33/86 |

OTHER PUBLICATIONS

Mischke et al. (2003) Veterinary J. 165(1): 43-53.*
Bin et al. (2002) J. Med. Chem. 45: 5694-5709.*
Malinin, A. et al., "Monitoring platelet inhibition after clopidogrel with the VerifyNow-P2Y12® rapid analyzer: The VERIfy Thrombosis risk ASsessment (VERITAS) study," Thrombosis Research, 119(3):277-84 (2007) (Epub Mar. 24, 2006).
Coleman B., "Platelet inhibition monitoring implications for POCT," Oral Presentation of Feb. 8, 2006, Internet document, address: www.pointofcare.net/NewYork/Feb82006Meeting.htm.
Mischke et al.; "Influence of Platelet Count, Acetylsalicylic Acid, Von Willebrand's Disease, Coagulopathies, and Haematocrit on Results Obtained Using a Platelet Function Analyser in Dogs"; The Veterinary Journal, vol. 165, No. 1, pp. 43-52 (2003).
Xu et al.; "Acyclic Analogues of Adenosine Bisphosphates as P2Y Receptor Antagonists: Phosphate Substitution Leads to Multiple Pathways of Inhibition of Platelet Aggregation"; Journal of Medicinal Chemistry, American Chemical Society, vol. 45, pp. 5694-5709 (2002).
Sigma-Aldrich; Cell Signaling & Neuroscience; "First $P2Y_{12}$ Receptor Antagonist Available from Sigma-RBI", Prod. No. M5942, 1 page (2007).
Judge et al.; Abstract of "Incomplete $P2Y_{12}$ Receptor Blockade by Clopidogrel is not Due to the Presence of an Internal Pool of $P2Y_{12}$ Receptors"; Journal of Thrombosis and Haemostasis, vol. 3, No. Supplement 1, 1 page (Aug. 2005).
Wiviott et al.; Randomized Comparison of Prasugrel (CS-747, LY640315), A Novel Thienopyridine $P2Y_{12}$ Antagonist, with Clopidogrel in Percutaneous Coronary Intervention: Results of the Joint Utilization of Medications to Block Platelets Optimally (JUMBO)-TIMI 26 Trial; Circulation, vol. 111, pp. 3366-3373 (2005).
Kam et al.; "The Thienopyridine Derivatives (Platelet Adenosine Diphosphate Receptor Antagonists), Pharmacology and Clinical Developments"; Anaesthesia, vol. 58, pp. 28-35 (2003).
Houston et al.; "[$^{32}$P]2-Iodo-$N^6$-Methyl-(N)-Methanocarba-2'-Deoxyadenosine-3',5'-Bisphosphate ([$^{32}$p]MRS2500), A Novel Radioligand for Quantification of Native $P2Y_1$ Receptors"; British Journal of Pharmacology, vol. 147, No. 5, pp. 459-467 (2006).

(Continued)

Primary Examiner — Lisa J Hobbs
(74) Attorney, Agent, or Firm — Finnegan, Henderson, Farabow, Garrett & Dunner, LLP

(57) ABSTRACT

The invention lies in the area of platelet function diagnostics and relates to a method for the determination of platelet function under flow conditions as well as a device for the implementation of this method. The method is particularly suitable for the determination of the effect of clopidogrel and of other P2Y(12) antagonists with antithrombotic activity as well as the determination of P2Y(1) antagonists with antithrombotic activity.

9 Claims, 3 Drawing Sheets

(56) References Cited

OTHER PUBLICATIONS

André et al.; "Anticoagulants (Thrombin Inhibitors) and Aspirin Synergize with $P2Y_{12}$ Receptor Antagonism in Thrombosis"; Circulation, vol. 108, pp. 2697-2703 (2003).
Jin et al.; "Adenosine Diphosphate (ADP)-Induced Thromboxane $A_2$ Generation in Human Platelets Requires Coordinated Signaling Through Integrin $\alpha_{iib}\beta_3$ and ADP Receptors"; Hemostasis, Thrombosis, and Vascular Biology, Blood, vol. 99, No. 1, pp. 193-198 (2002).
Fattorutto M., "Evaluation of platelet aggregation in flow and platelet aggregometry during pregnancy," Br J Anaesth., 90(2):252 (2003).
Harrison P. et al., "Screening for aspirin responsiveness after transient ischemic attack and stroke," Stroke, 36(5):1001-5 (2005).
Lordkipanidzé M. et al., "Comparison of four tests to assess inhibition of platelet function by clopidogrel in stable coronary artery disease patients," Eur Heart J., 29(23):2877-85 (2008).
Rand M.L. et al., "Platelet function assays," Transfus Apher Sci., 28(3):307-17 (2003).
Vincelot A. et al., "Platelet function during pregnancy: an evaluation using the PFA-100 analyser," Br. J. Anaesth., 87(6):890-3 (2001).
Kozek-Langenecker et al.; "Lokoregionalanasthesien Unter Gerinnungshemmender Medikation"; Anaesthesist, vol. 54, No. 5, pp. 476-484, (2005).
Fattorutto, M., Br. J. Anaesth., 90(2):252 (2003).
Rand M.L., et al., Transfus. Apher. Sci., 28(3):307-17 (2003).
Harrison P. et al., Stroke, 36(5):1001-5 (2005).
Lordkipanidzé M., Eur. Heart J., 29:2877-85 (2008).

\* cited by examiner

METHOD AND DEVICE FOR THE DETERMINATION OF PLATELET FUNCTION UNDER FLOW CONDITIONS

This application is a division of U.S. application Ser. No. 11/790,853, filed Apr. 27, 2007, and claims the benefit of priority under 35 U.S.C. §119 to German Patent Application No. DE 10 2006 020 385.2, filed on Apr. 28, 2006, incorporated herein by reference.

The invention lies in the area of platelet function diagnostics and relates to an in vitro method for the determination of platelet function under flow conditions as well as a device for the implementation of this method. The method is particularly suitable for the determination of the effect of clopidogrel after oral intake and of other P2Y(12) antagonists with antithrombotic activity. Furthermore, the blockade of the second platelet ADP receptor (P2Y(1) receptor) by specific antagonists can also be detected with the method.

Physiological processes that on the one hand guarantee the fluidity of blood in the vascular system and on the other avoid extravascular blood loss through the formation of blood clots are classified under the term hemostasis. Numerous protein factors are involved in the regulation of hemostasis as well as also cellular components, for example thrombocytes (platelets). In the case of vessel damage attachment of platelets to the subendothelial collagen first takes place. This adhesion is mediated by adhesion proteins such as the von Willebrand factor (VWF). During the adhesion process the platelets are activated and release mediators from their granulae through which the aggregation of further platelets and an increase in activation are induced. In this way primary vessel wall occlusion (primary hemostasis) takes place which then is further stabilized by reactions of the plasmatic coagulation system (secondary hemostasis). Dysregulation of these processes can lead to thrombophilia or a tendency towards hemorrhage, which dependent upon the degree of severity can have life-threatening consequences.

Different in vitro test methods have been developed in coagulation diagnostics which help to determine whether the blood of a patient coagulates properly or whether a coagulation defect is present. In the case of a coagulation defect it is frequently necessary to obtain precise information on the cause of the defect present in order to be able to select the optimal therapeutic measures. An important sub-function of the coagulation system that can be investigated specifically is primary hemostasis, which is essentially dependent on the functionality of the platelets.

Methods to determine platelet function are not only used for the diagnosis of acquired or inherited platelet dysfunction, but also for monitoring antithrombotic therapies. Medication that inhibits the aggregation of platelets is used mainly for the prophylaxis and therapy of arterial thromboembolitic events such as myocardial infarction or stroke. The most widely used active compounds with platelet aggregation inhibitory effect are acetylsalicylic acid (ASA) and the thienopyridines clopidogrel and ticlopidine. ASA irreversibly inhibits cyclooxygenase-1 (COX-1), an intracellular enzyme that is involved in the synthesis of the platelet aggregation promoter thromboxane A2. Owing to their mode of action clopidogrel and ticlopidine belong to the class of P2Y(12) antagonists. After oral intake of clopidogrel or ticlopidine metabolites are formed in the liver that block selectively the purinergic P2Y(12) receptor. The purinergic P2Y(12) receptor is expressed on the platelet surface and can be activated by extracellular adenosine-5'-diphosphate (ADP). As a consequence of the activation of the purinergic P2Y(12) receptor intracellular processes are induced in the platelets, for example the inhibition of the formation of cAMP, that give rise to a platelet aggregation reaction. P2Y(12) antagonists block the purinergic P2Y(12) receptors on the platelet surface and thus possess an antithrombotic activity.

The second purinergic ADP receptor P2Y(1) is also expressed on the platelet surface and is activated by extracellular adenosine-5'-diphosphate. As a consequence of the activation of the purinergic P2Y(1) receptor intracellular processes are initiated in the platelets, for example an increase in intracellular calcium, that give rise to a platelet aggregation reaction. P2Y(1) receptor antagonists act against this process and thus have an antithrombotic activity.

Precise knowledge of the status of the platelet function of patients who are receiving antithrombotic therapy is considered to be increasingly important since, for example, the occurrence of so-called clopidogrel resistance is under serious consideration as an increasing risk factor. Clopidogrel resistance is present when the platelet function of a patient is only slightly influenced by the administration of a standard dose of clopidogrel, or not at all. On the one hand a test can be carried out to determine whether an adequate antithrombotic response is actually achieved with a selected dose by determination of platelet function. On the other hand, doses or responses of an antithrombotic medication that are too high can be determined and treated, which is necessary, for example, prior to surgery in order to exclude bleeding complications.

Different methods for the investigation of platelet function are known in the prior art. Bleeding time determination is a global in vivo test which records primary hemostasis. The bleeding time is determined wherein the patient is given a small cut or prick injury and the time for coagulation is measured. It is a poorly standardizable, coarsely informative test that is used primarily in an emergency situation in order to obtain an overview of primary hemostasis. Taking platelet aggregation inhibitors leads to an increase in bleeding time. The disadvantage of bleeding time determination is that platelet dysfunction cannot be excluded even with a normal bleeding time.

Different in vitro methods allow a significantly more sensitive detection of platelet dysfunction. Normally in these methods platelet aggregation is induced in a whole blood sample or in a sample of platelet-rich plasma (PRP) by the addition of an activator and the aggregation reaction is measured. The most commonly used activators used for the induction of platelet activation are ADP (adenosine-5'-diphosphate), collagen, epinephrine (adrenaline), ristocetin and different combinations thereof as well as thrombin, TRAP (thrombin receptor activating protein) or serotonin.

In light transmission aggregometry, also known as Born platelet aggregation, the aggregation efficiency of platelets in platelet-rich plasma is measured photometrically in the presence of aggregation-inducing compounds in an aggregometer. The light transmission of the PRP sample is increased due to aggregate formation so that the rate of aggregate formation, for example, can be determined by measurement of light transmission. The therapeutic effects of platelet aggregation inhibitors used medically can also be determined with the aid of light transmission aggregometry. A disadvantage of light transmission aggregometry is that only platelet-rich plasma can be used as sample material. Platelet-rich plasma lacks not only important blood components such as, for example, red and white blood cells, but also requires a time-consuming and error-prone sample preparation.

Another test principle for the determination of platelet function is realized in the Platelet Function Analyzer (PFA-100®, Dade Behring Marburg GmbH, Marburg, Germany). The PFA-100® is a global, automated and standardized in vitro whole blood test with which primary hemostasis is measured under flow conditions and thus in the presence of high shear forces. In order to simulate the flow conditions and the shear forces that prevail in the smaller arterial blood vessels a partial vacuum of about −40 mbar is produced in a special test cartridge. The citrated whole blood that is located in a sample reservoir is sucked through a capillary with a diameter of about 200 μm. The capillary leads into a measurement chamber which is closed with a partition member, for example a membrane, which has a central capillary opening (aperture) through which the blood flows due to the partial vacuum. In most cases the membrane, at least within the region surrounding the aperture, is coated with one or more activators that induce platelet aggregation so that the passing blood comes into contact with the aggregation-inducing substances in the region of the aperture. As a consequence of the induced adhesion and aggregation of the platelets a thrombus is formed in the region of the aperture which seals the membrane opening and stops the blood flow. In this system the time required to close the membrane opening is measured. This so-called closure time correlates with the functional efficiency of the platelets. A test cartridge for use in a method for the determination of platelet function based on the closure time is described, for example, in patent specification WO 97/34698. Thus far test cartridges that are equipped with a membrane that is coated with collagen (Col) and also with either ADP or epinephrine (Epi) are used in the method for the determination of closure time. Different partition members as well as their preparation and use are described, for example in patent specification EP 716 744 B1.

Subject to the construction, a distinction is thus made between Col/ADP test cartridges and Col/Epi test cartridges. Normally a patient sample is first analyzed with the aid of a Col/Epi test cartridge. In the case of an abnormally prolonged Col/Epi closure time, which indicates a disorder of platelet aggregation, a Col/ADP measurement is subsequently carried out. If the Col/ADP closure time is likewise abnormally prolonged this is an indicator of platelet dysfunction or a disorder of the von Willebrand factor. If in contrast the Col/ADP closure time is normal this can indicate the presence of acetylsalicylic acid or the presence of an acquired or inherited thrombocytopathy such as, for example, storage pool disease. A disadvantage of the PFA-100® system is that the available Col/ADP and Col/Epi test cartridges have only a limited sensitivity for the aggregation inhibitory effect of platelet aggregation inhibitors of the thienopyridine group (e.g. clopidogrel, ticlopidine). A more reliable determination of the therapeutic effect of the medically used clopidogrel and ticlopidine, especially when the patient has also taken ASA (e.g. Aspirin®) is hitherto not possible with the help of the known Col/ADP and Col/Epi test cartridges in the PFA-100® system.

The patent specification WO 2005/007868 A2 describes an alternative method for the determination of platelet function that allows the detection of the therapeutic effect of clopidogrel and other P2Y(12) antagonists. In this method a whole blood sample of a patient is mixed with an anticoagulant and treated with ADP for the induction of platelet aggregation. In addition, prostaglandin E1 (PGE 1) is added to the sample. Prostaglandin E1, a product of human arachidonic acid metabolism, is able to reduce the reactivity of platelets significantly, even in low doses, and is therefore also used for the inhibition of platelet activation. In the test method described in WO 2005/007868 A2, PGE 1 is used to reduce the undesirable activation of the ADP receptor P2Y (1) and thus to increase the specificity of the test method for the P2Y(12) receptor and for P2Y(12) antagonists such as clopidogrel. In addition, microparticles to which a ligand for the GPIIb/IIIa receptor such as, for example, fibrinogen is coupled, are added and the aggregation reaction is measured aggregometrically on the basis of the increasing light transmission. A disadvantage of the previously described method is that as with light transmission aggregometry platelet function is not determined under the influence of flow conditions and shear forces.

SUMMARY OF THE INVENTION

The object forming the basis of the present invention is to provide a method for the determination of platelet function under flow conditions that allows the determination of the platelet aggregation inhibitory effect of P2Y(12) antagonists. The solution to the object lies in the provision of the methods and materials according to the invention described in the claims.

The object of the present invention is an in vitro method for the determination of platelet function in a whole blood sample. Preferably the whole blood sample is freshly drawn anticoagulated venous human or animal blood that is to be investigated within four hours after blood collection with the help of the method according to the invention. The whole blood is preferably anticoagulated by the addition of an anticoagulant. Suitable for use as anticoagulant are buffered calcium-binding citrate solutions such as, for example, 3.2 or 3.8% buffered sodium citrate solutions, as well as natural or synthetic direct thrombin inhibitors such as, for example, hirudin, PPACK (D-Phe-Pro-Arg-chloromethylketone, HCl), argatroban and melagatran, or natural or synthetic direct Factor Xa inhibitors such as, for example, antistasin, tick anticoagulant peptide, yagin, draculin, GGACK (H-Glu-Glu-Arg-chloromethylketone), diamidino Factor Xa inhibitors and monobenzamidine Factor Xa inhibitors.

DETAILED DESCRIPTION OF THE INVENTION

The method according to the invention for the determination of platelet function comprises several methodological steps. For the simulation of the physiological flow conditions prevailing in small arteries the blood that is initially located in a reservoir is passed though a capillary that preferably has a diameter of about 200 μm. The capillary leads into a measurement chamber that is separated into two compartments by a partition member. The partition member has an opening through which the blood is passed from the first into the second compartment. The method of the invention is characterized in that the artition member used comprises an activator of puringeric receptors and an activator of intracellular adenylate cyclases whereby the blood flowing through the opening of the partition member is brought into contact with these substances contained in or on the partition member. As a result of the platelet aggregation that is induced by the contact with the substances a thrombus forms at the opening of the partition member. The time that is necessary for the formation of the thrombus at the opening of the partition member up to closure of the opening is measured. Preferably the closure time is measured in that an apparatus is used that comprises a pressure sensor which determines the blood flow through the aperture during the test. Thus, after initial rapid aspiration of the dead volume of the test cartridge the initial flow rate is first determined. If the flow rate falls below 10% of this initial flow rate for more than 3 seconds the measurement is ended and the time passed until then is recorded as the so-called closure time. This so-called closure time, which is i.a. dependent on the aggregation reaction of the stimulated platelets, is a measure of platelet function. Preferably the closure time that was measured for a whole blood sample of a patient is compared with a closure time reference range for whole blood samples of healthy subjects.

Preferably the blood flow through the capillary and through the opening of the partition member is produced by creating a partial vacuum in the measurement chamber, that is by suction. In a particularly preferred embodiment the partial vacuum is produced by the combined action of a suitable test cartridge and an apparatus. An example of such a system is described, for example, in patent specification WO 97/034698.

The partition member used in the method according to the invention comprises an activator of purinergic receptors, preferably from the group adenosine-5'-diphosphate (ADP), 2-methylthioadenosine-5'-diphosphate (2-MeSADP) and their derivatives. In a preferred embodiment a partition member is used that comprises an ADP salt or a 2-MeSADP salt. In a preferred embodiment a partition member is used that comprises 1 to 100 µg, especially preferred 5 to 50 µg, particularly preferred 20 to 25 µg ADP.

The partition member used comprises further an activator of intracellular adenylate cyclases, preferably from the group prostaglandin E1 (PGE 1), forskolin and its water-soluble derivatives, prostaglandin 12 and its stable derivatives, iloprost and cicaprost. In a preferred embodiment a partition member is used that comprises 1 to 1000 ng, especially preferably 3 to 20 ng prostaglandin E1. In another preferred embodiment a partition member is used that comprises 0.1 to 10 µg, especially preferred 0.5 to 5 µg forskolin.

In an especially preferred embodiment of the method a partition member is used that comprises ADP and prostaglandin E1.

In a further preferred embodiment of the method according to the invention a partition member is used that also comprises calcium ions, preferably in the form of calcium chloride dihydrate. In a preferred embodiment a partition member is used that comprises 50 to 200 µg, especially preferred 100 to 150 µg, most especially preferred 125 µg calcium ions in the form of calcium chloride dihydrate.

It was found that in the presence of calcium ions the platelet aggregation inhibitory effect of acetylsalicylic acid (ASA) is reduced so considerably that an accurate determination of the platelet aggregation inhibitory (antithrombotic) effect of other platelet aggregation inhibitors such as, for example, P2Y(12) antagonists such as clopidogrel is also possible in such samples that comprise ASA. A partition member that comprises calcium ions is thus especially then to be used in the method according to the invention when the whole blood sample to be investigated is anticoagulated with a calcium-binding anticoagulant. If the whole blood sample to be investigated is anticoagulated with a non-calcium-binding anticoagulant such as, for example, with a direct thrombin or Factor Xa inhibitor, the calcium ion concentration contained endogenously in the sample is sufficient to reduce an ASA-induced platelet dysfunction. Nevertheless, a partition member that comprises calcium ions can also be used in these cases.

The method according to the invention is used most preferably for the determination of the antithrombotic (platelet aggregation inhibitory) effect of a P2Y(12) antagonist, especially for the determination of a P2Y(12) antagonist from the group clopidogrel, ticlopidine, prasugrel (synonym: CS-747) and other thienopyridines, AR-C67085MX (2-propylthio-D-β,γ-dichloromethylene-adenosine-5'-triphosphate), cangrelor (synonym: AR-C69931MX, N6-[2-methylthio)ethyl]-2-(3,3,3-trifluoropropyl)thio-5'-adenylic acid), C1330-7 (N1-(6-ethoxy-1,3-benzothiazol-2-yl-2-(7-ethoxy-4-hydroxy-2,2-dioxo-2H-2-6benzo[4,5][1,3]thiazole[2,3-c][1,2.4]thiadiazin-3-yl)-2-oxo-1-ethanesulfonamide), AZD 6140 (nucleoside analogs), MRS 2395 (2,2-dimethyl-propionic acid 3-(2-chloro-6-methylaminopurin-9-yl)-2-(2,2-dimethyl-propionyloxymethyl)-propyl ester) and 2-MeSAMP (2-methylthioadenosine-5'-monophospate).

Surprisingly, it was also found that the method according to the invention can also be used for the determination of the antithrombotic (platelet aggregation inhibitory) effect of a P2Y(1) antagonist. In particular, the method can be used for the determination of the antithrombotic effect of P2Y(1) antagonists from the group MRS 2179 [2'-deoxy-N6-methyladenosine-3',5'-bisphosphate, diammonium salt], MRS 2279 [(N)-methanocarba-N6-methyl-2-chloro-neoxyadenosine-3',5'-diphosphate], MRS 2500 [2-iodo-N6-methyl-(N)-methanocarba-2'-deoxyadenosine-3'5'-diphosphate], A2P5P [adenosine-2',5'-diphosphate], A3P5P [adenosine-3',5'-diphosphate], A3P5PS [adenosine-3'-phosphate-5'-phosphosulfate].

A further object of the present invention concerns a device, as for example a test cartridge, which is suitable for the determination of platelet function in a whole blood sample wherein the device comprises different elements: a) a reservoir for storing the sample; b) a capillary through which the blood is passed from the reservoir into a measurement chamber; c) a measurement chamber that is separated into two compartments by a partition member, wherein the first compartment receives the blood from the capillary; d) a partition member which divides the measurement chamber into two compartments and which has an opening through which the blood can flow from the first compartment into the second compartment. The device is characterized in that the partition member comprises an activator of purinergic receptors and an activator of intracellular adenylate cyclases. In one preferred embodiment the partition member also comprises calcium ions, preferably in the form of calcium chloride dihydrate.

The partition member is a porous or nonporous support matrix for an activator of purinergic receptors and an activator of intracellular adenylate cyclases and optionally for calcium ions. Preferably the partition member is constructed in the form of a membrane. The preferred material is liquid absorbing so that the aforementioned substances can be applied in solution. Especially preferred materials are cellulose esters, ceramic, nylon, polypropylene, polyether sulfone, and polyvinylidene fluoride (PVDF). Preferably the partition member wetted or soaked with the desired substances is dried. By contact of the blood with the partition member the substances are dissolved from the partition member and mix with the blood sample.

The partition member preferably has a circular opening that is produced in the support matrix by punching. The diameter of the opening in the partition member is so dimensioned that a thrombus can form under the conditions of the respective method which closes the opening and can thus stop the blood flow. Preferably the opening in the partition member has a diameter between approximately 100

μm and approximately 200 μm. Particularly preferably the diameter of the opening in the partition member is about 100 μm.

The device according to the invention is preferably so constructed that a partial vacuum that brings about a blood flow from the reservoir through the capillary into the measurement chamber and through the opening of the partition member is produced in the device with the help of an apparatus that is integrated with components of the device.

The present invention further relates to the use of a device according to the invention in a method for the determination of platelet function. A preferred use of a device according to the invention relates to the use for the determination of the antithrombotic effect of a P2Y(12) antagonist. Another preferred use of a device according to the invention relates to the use for the determination of the antithrombotic effect of a P2Y(1) antagonist.

The following embodiment examples serve to illustrate the method according to the invention and are not to be understood as limiting.

BRIEF DESCRIPTION OF THE DRAWINGS

FIG. 1 shows by way of example how a device for the determination of platelet function according to the invention can be constructed. Shown is a test cartridge in accordance with WO 97/34698 in longitudinal section that is placed in a suitable apparatus for implementing the method according to the invention and into which extends a vacuum apparatus (15) that is responsible for the generation of the partial vacuum The vacuum apparatus (15) has a ring gasket (27) which is located as a seal on the circumferential edge (12) of the sample container (10). The test cartridge has a housing that forms a reservoir (61) and a test chamber (63). The test chamber (63) is constructed to accept a sample container (10) the cavity of which can also be referred to as measurement chamber. The sample container (10) supports a partition member (6) treated with reagents and with a central opening (aperture) and a capillary attachment (30, 31) that connects the capillary (40) with the sample container (10). Reservoir (61) and test chamber (63) are separated by a penetrable element (70). The figure shows a phase of the test cycle after the vacuum apparatus (15) is in contact with sample container (10) and has moved downwards so that the base of the sample container (10) is in contact with the support (71) and the capillary (40) has penetrated the penetrable element (70) and penetrated into the sample (11). The apparatus produces a partial vacuum in the sample container (10) by means of which the sample (11) is pulled through the capillary (40) into the first compartment (18) of the measurement chamber and then through the opening in the partition member (6).

Figure 1:
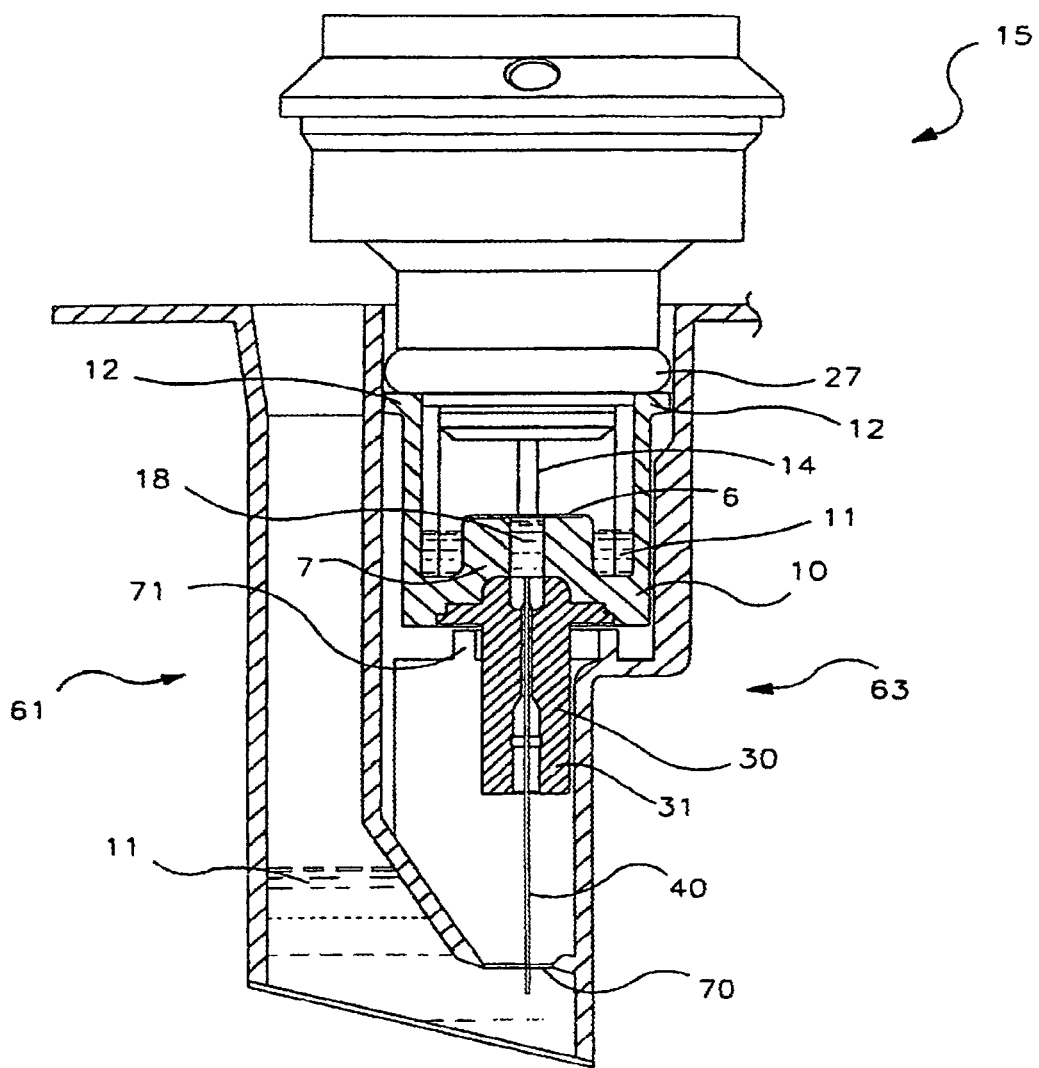
FIG. 1

Diagram for the illustration of closure times (in seconds [s]) for normal untreated whole blood samples (control) and for whole blood samples that had been treated with the P2Y(12) antagonist MRS 2395 and/or the COX-1 inhibitor acetylsalicylic acid (ASA) in vitro (see Example 2). Whole blood samples from 11 healthy donors anticoagulated with sodium citrate were used. On the left of the diagram are shown the mean values and the standard deviations of the closure times determined with the ADP/PGE1/calcium test cartridge according to the invention (cut-off: 81 seconds). On the right of the diagram are shown the mean values and the standard deviations of the closure times that were determined for comparison with conventional Col/Epi test cartridges (cut-off: 158 seconds). A comparison of the two types of test cartridge shows that with use of an ADP/PGE1 test cartridge according to the invention, closure times that lie significantly above the upper reference value (cut-off) were measured with samples that were treated with the P2Y(12) antagonist MRS 2395, whereas the same samples with the use of a Col/Epi test cartridge lie to a greater extent below the upper reference value (cut-off). That means that the method for determination of platelet function according to the invention allows a more sensitive determination of platelet dysfunction induced by a P2Y(12) antagonist than the comparison method from the prior art.

FIG. 3

Diagram for illustration of the closure times (in seconds [s]) for normal untreated whole blood samples (control) and for whole blood samples treated in vitro with the P2Y(12) antagonist MRS 2395, the P2Y(1) antagonist MRS 2179 or the COX-1 inhibitor acetylsalicylic acid (ASA) (see example 4). Whole blood samples from 10 healthy donors anticoagulated with P PACK were used. In the diagram are shown the mean values and the standard deviations of the closure times that were determined with the ADP/PGE1 test cartridges according to the invention (cut-off: 90 seconds). The performance evaluation shows that with use of an ADP/PGE1 test cartridge according to the invention, closure times that lie significantly above the reference value (cut-off) were measured with samples that were treated with the P2Y(12) antagonist MRS 2395 or the P2Y(1) antagonist MRS 2179, whereas the samples treated with COX-1 inhibitor acetylsalicylic acid show no prolongation of closure times and thus lie below the cut-off.

EXAMPLES

Example 1: Preparation of an ADP/PGE1/Calcium Test Cartridge According to the Invention For the preparation of a partition member for a test cartridge according to the invention a polyether sulfone filter membrane (Supor® membrane, Pall GmbH, Dreieich, Germany) was cut into strips. 1 μL of a solution comprising 7 μg/μL ADP (adenosine-5'-diphosphate potassium salt.2H$_2$O, Sigma-Aldrich Chemie GmbH, Steinheim, Germany) and 5 ng/μL PGE1 (prostaglandin E1, Sigma-Aldrich Chemie GmbH, Steinheim, Germany) and 367.5 μg/μL CaCl$_2$.2H$_2$O (equivalent to 100 μg/μL Ca$^{2+}$ ions) were pipetted punctiform onto the membrane and the membrane was dried. Next a circular opening (aperture) with a diameter of 100 μm was punched out of the middle of the region of the membrane treated with the reagents. The membrane thus prepared was used as partition member in the measurement chamber of a PFA-100® test cartridge (Dade Behring Marburg GmbH, Marburg, Germany).

Example 2: Use of an ADP/PGE1/Calcium Test Cartridge According to the Invention for the Determination of the Antithrombotic Effect of a P2Y(12) Antagonist In Vitro 2a) Sample Preparation Venous blood was taken from 11 healthy donors and anticoagulated with sodium citrate (3.2% buffered Na citrate).

Aliquots of the citrated whole blood sample were treated in vitro with the P2Y(12) antagonist MRS 2395 (Sigma-Aldrich Chemie GmbH, Steinheim, Germany). For this purpose an ethanolic MRS 2395 stock solution (15 mg/mL)

was mixed with the whole blood samples so that an end concentration of 100 µmol/L was obtained.

Further aliquots of the citrated whole blood samples were treated in vitro with the COX-1 inhibitor acetylsalicylic acid (abbr.: ASA; Sigma-Aldrich Chemie GmbH, Steinheim, Germany). For this purpose an aqueous ASA stock solution (1 mg/mL) was mixed with whole blood samples so that an end concentration of 30 µmol/L was obtained.

Further aliquots of the citrated whole blood samples were treated in vitro with MRS 2395 and with ASA so that the previously stated end concentrations were achieved.

After addition of the reagents the blood samples were incubated at room temperature for 5 minutes.

2b) Determination of the Antithrombotic Effect of MRS 2395 by ADP Induced Light Transmission Aggregometry (According to Born)

In order to check whether the samples treated with MRS 2395 actually show a reduced platelet aggregation, platelet rich (PRP) and platelet poor (PPP) plasma was prepared from aliquots of the untreated and MRS 2395-treated whole blood samples described under Example 2a), and the samples were then treated with 2 µM ADP. The PPP samples were used as blank controls. The photometric measurement of the aggregation reaction was carried out in the automated coagulation apparatus BCT® (Dade Behring Marburg GmbH, Marburg, Germany) under continuous stirring (600 rpm). The platelet aggregation of the samples treated with MRS 2395 was reduced by a mean of 27% compared with the platelet aggregation of the untreated samples.

2c) Determination of the Antithrombotic Effect of MRS 2395 by the Method According to the Invention Under Flow Conditions To determine the closure time as a measure of platelet function the whole blood samples described under Example 2a) were investigated with the aid of the ADP/PGE1/calcium test cartridge according to the invention described in Example 1 in a PFA-100® apparatus (Platelet Function Analyzer-100, Dade Behring Marburg GmbH, Marburg, Germany). For this purpose 700 µL of a blood sample were placed in the reservoir of the temperature equilibrated test cartridge (+37° C.) and incubated at +37° C. for 3 minutes. Next a partial vacuum of −40 mbar was generated by the apparatus by which means the blood was sucked through a capillary from the reservoir (diameter 200 µm) and finally through an opening (aperture) of the partition member in the measurement chamber. The time required up to the closure of the aperture by formation of a blood clot was determined as closure time. Every sample investigated was determined in duplicate and the mean value of a duplicate determination was used as the measurement value.

For comparison purposes the whole blood samples described under Example 2a) were investigated in parallel with a known Col/Epi PFA-100® test cartridge (2 µg collagen and 10 µg epinephrine on the membrane; 150 µm aperture diameter; Dade Behring Marburg GmbH, Marburg, Germany) in the PFA-100® apparatus.

Figure 2:
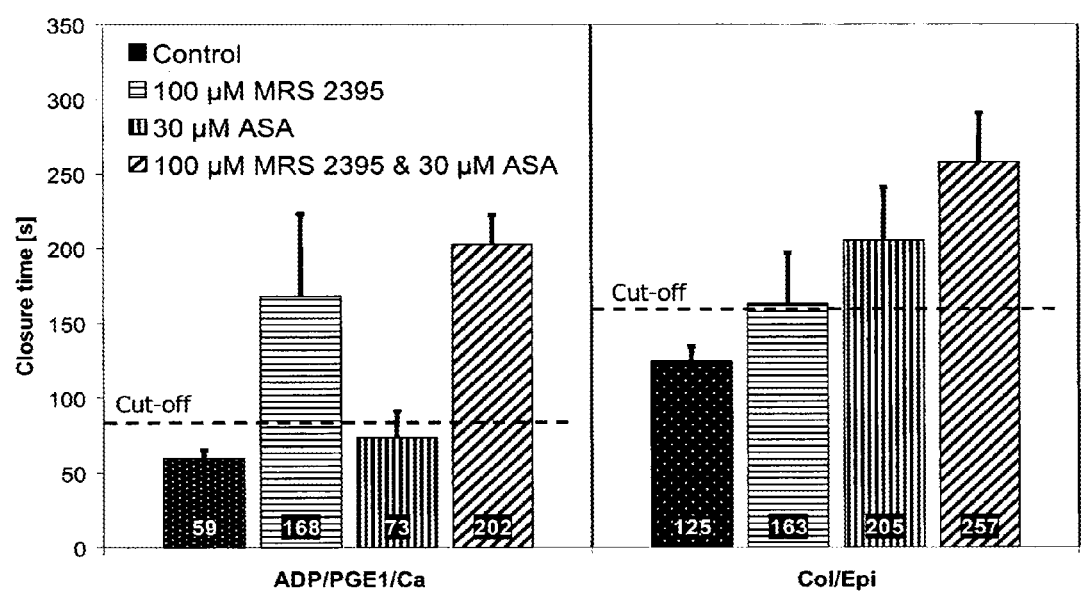
FIG. 2

The results of the investigations are summarized in FIG. 2 and the relevant figure description.

In Table 1 details are reported for how many of the respective 11 MRS 2395- and/or acetylsalicylic acid-treated samples a closure time above the cut-off was measured with the aid of the ADP/PGE1 test cartridge according to the invention and with the conventional Col/Epi test cartridge. In 9 of the 11 samples treated with MRS 2395 an abnormally reduced platelet aggregation was measured with the aid of the method according to the invention, whereas only 4 of 11 samples were classified as abnormal with the aid of the conventional method. That means that the method according to the invention has an increased sensitivity for a platelet dysfunction induced by a P2Y(12) antagonist. Moreover, it is of advantage that in the presence of free calcium ions the method according to the invention has a very low sensitivity for acetylsalicylic acid. In only one of 11 acetylsalicylic acid-treated samples, an abnormally reduced platelet aggregation is measured with the aid of the method according to the invention, whereas, in contrast, with the conventional Col/Epi test cartridge 8 of the 11 samples treated with acetylsalicylic acid were determined as abnormal. Samples that are treated with MRS 2395 and acetylsalicylic acid are classified 100% as abnormal with the aid of the conventional method, whereas only 9 of the 11 samples (as with sole addition of MRS 2395) are classified as abnormal with the method according to the invention. Thus on the basis of its high sensitivity for platelet dysfunction induced by P2Y(12) antagonists and its low sensitivity to platelet dysfunction induced by acetylsalicylic acid, the method according to the invention is suitable for differentiation of the two classes of antithrombotics.

TABLE 1

| | Number of samples with closure times above cut-off (n = 11) Sample | | |
|---|---|---|---|
| Test cartridge | MRS 2395 (P2Y(12) antagonist) | Acetylsalicylic acid (COX-1 inhibitor) | MRS 2395 + Acetylsalicylic acid |
| ADP/PGE1 | 9 | 1 | 9 |
| Col/Epi | 4 | 8 | 11 |

2d) Determination of the Reference Range for Col/Epi and ADP/PGE1 Test Cartridges Venous blood was taken from healthy donors and anticoagulated with sodium citrate (3.2% buffered Na citrate). The closure time determination was carried out for each whole blood sample in the PFA-100® apparatus. Samples from 186 donors were determined in duplicate with a Col/Epi PFA-100® test cartridge [see Example 2c]. Samples from 159 donors were determined in duplicate with an ADP/PGE1/calcium test cartridge according to the invention [see Examples 1 and 2c)].

The reference ranges (normal range) for the Col/Epi closure time and the ADP/PGE1 closure time were established in that the measurement value ranges in which 90% of the measurement values found for the healthy subjects lay were determined (90% central interval of the normal distribution of all measurements). This gave the following reference ranges for the closure times:

| Col/Epi | 70-158 seconds |
|---|---|
| ADP/PGE1 | 46-81 seconds. |

The upper reference limit of the reference range was defined as cut-off, i.e. as threshold value, for a platelet dysfunction. If the closure time of a patient sample deviates from the reference range it can indicate a platelet dysfunction. This means Col/Epi closure times that are greater than 158 seconds and ADP/PGE1 closure times that are greater than 81 seconds indicate the presence of a platelet dysfunction within the sense of a reduced aggregation efficiency.

Example 3: Use of an ADP/PGE1 Test Cartridge According to the Invention for the Determination of the Antithrombotic Effect of the P2Y(12) Antagonist Clopidogrel Ex Vivo Venous blood was taken from 13 patients suffering from peripheral arterial obstructive disease and who had been treated with a daily dose of 75 mg clopidogrel (Piavix®, Sanofi-Aventis) as sole antithrombotic for a period of at least 4 weeks and the blood was anticoagulated with sodium citrate (3.8 buffered Na citrate). The samples were investigated with the aid of different methods to determine platelet function.
1. according to the invention under flow conditions and use of an ADP/PGE1/calcium PFA-100® test cartridge (see Examples 1 and 2c), cut-off: >81 seconds;
2. under flow conditions and use of a PFA-100® test cartridge that differed from the test cartridge according to the invention in accordance with Example 1 in that it comprised no PGE1, cut-off: >78 seconds;
3. with ADP-induced light transmission aggregometry (according to Born) with addition of 2 μM ADP (see Example 2b), cut-off: <40% light transmission at end of test;
4. with ADP-induced light transmission aggregometry (according to Born) with the addition of 5 μM ADP (see example 2b), cut-off: <40% light transmission at end of test. This method is recommended by Sanofi-Aventis, the manufacturer of the clopidogrel preparation Plavix®, for the determination of the antithrombotic effect of the medicament.

The cut-offs for the individual test procedures were determined by preliminary investigations with whole blood and plasma samples of normal donors.

Table 2 presents in detail with which of the four methods in which of the 13 patient samples an antithrombotic effect of clopidogrel could be detected. "+" means an antithrombotic effect could be detected. "−" means no antithrombotic effect could be detected. "0" means that the duplicate determination gave contradictory results, i.e. one value above and one value below the cut-off.

TABLE 2

| Method | 1 | 2 | 3 | 4 | 5 | 6 | 7 | 8 | 9 | 10 | 11 | 12 | 13 | Sensitivity |
|---|---|---|---|---|---|---|---|---|---|---|---|---|---|---|
| 1.) ADP/PGE1 | − | 0 | + | + | + | − | + | + | + | + | + | + | + | 77% |
| 2.) ADP | − | − | + | + | + | − | − | − | + | − | + | − | + | 46% |
| 3.) Aggregometry 2 μM ADP | − | + | − | + | + | − | − | + | + | + | + | + | + | 69% |
| 4.) Aggregometry 5 μM ADP | − | − | − | + | + | − | − | + | + | + | + | + | + | 62% |

With the aid of the method of the invention the antithrombotic effect of clopidogrel intake could be detected in 10 of the 13 patients (77%). The duplicate determination gave contradictory results with one patient (patient no. 2), whilst with 2 patients (patient no. 1 and 6) no reduced platelet aggregation could be detected. However, in these two patients an effect of dosage of clopidogrel could not be detected in any of the methods used.

The method according to the invention is more sensitive towards the platelet dysfunction induced by clopidogrel than the standard method of ADP-induced light transmission aggregometry according to Born and more sensitive than the method with which a test cartridge is used that comprises ADP but no PGE1.

Example 4: Use of an ADP/PGE1 Test Cartridge According to the Invention for the Determination of the Antithrombotic Effect of a P2Y(12) and a P2Y(1) Antagonist In Vitro 4a) Sample Preparation Venous blood was taken from 10 healthy donors and anticoagulated with 75 μM PPACK.

Aliquots of the whole blood samples were treated in vitro with the P2Y(12) antagonist MRS 2395 (Sigma-Aldrich Chemie GmbH, Steinheim, Germany). For this purpose an ethanolic MRS 2395 stock solution (15 mg/mL) was mixed with the whole blood samples so that an end concentration of 150 μmol/L was obtained.

Further aliquots of the whole blood samples were treated in vitro with the COX-1 inhibitor acetylsalicylic acid (abbr. ASA; Sigma-Aldrich Chemie GmbH, Steinheim, Germany). For this purpose an aqueous ASA stock solution (1 mg/mL) was mixed with the whole blood samples so that an end concentration of 30 μmol/L was obtained.

Further aliquots of the whole blood samples were treated in vitro with the P2Y(1) antagonist MRS 2179 (Sigma-Aldrich Chemie GmbH, Steinheim, Germany). For this purpose an aqueous MRS 2179 stock solution (1 mg/ml) was mixed with the whole blood samples so that an end concentration of 75 μmol/L was obtained.

After addition of the reagents the blood samples were incubated at room temperature for 5 minutes.

4b) Determination of the Antithrombotic Effect of MRS 2395 and MRS 2179 with the Aid of the Method According to the Invention Under Flow Conditions For the determination of the closure time as a measure of the platelet function the whole blood samples described under Example 4a) were investigated with the aid of a ADP/PGE1 test cartridge according to the invention in a PFA-100® apparatus (Platelet Function Analyzer-100, Dade Behring Marburg GmbH, Marburg, Germany). The ADP/PGE1 test cartridge according to the invention used was prepared essentially as described in Example 1 but without the partition member having been treated with $CaCl_2 \cdot 2H_2O$. The test cartridge thus comprised 7 μg ADP and 5 ng PGE1 but no calcium ions.

700 μL of a blood sample was added to the reservoir of the temperature equilibrated test cartridge (+37° C.) and incubated at +37° C. in the apparatus for 3 minutes. Next a partial vacuum of −40 mbar was applied by the apparatus when the blood was sucked through a capillary (diameter 200 μm) from the reservoir and finally through an opening (aperture) of the partition member in the measurement chamber. The time that was required up to the closure of the aperture by formation of a blood clot was determined as closure time. Every sample investigated was determined in duplicate and the mean value of a duplicate determination was used as the measurement value.

Figure 3:
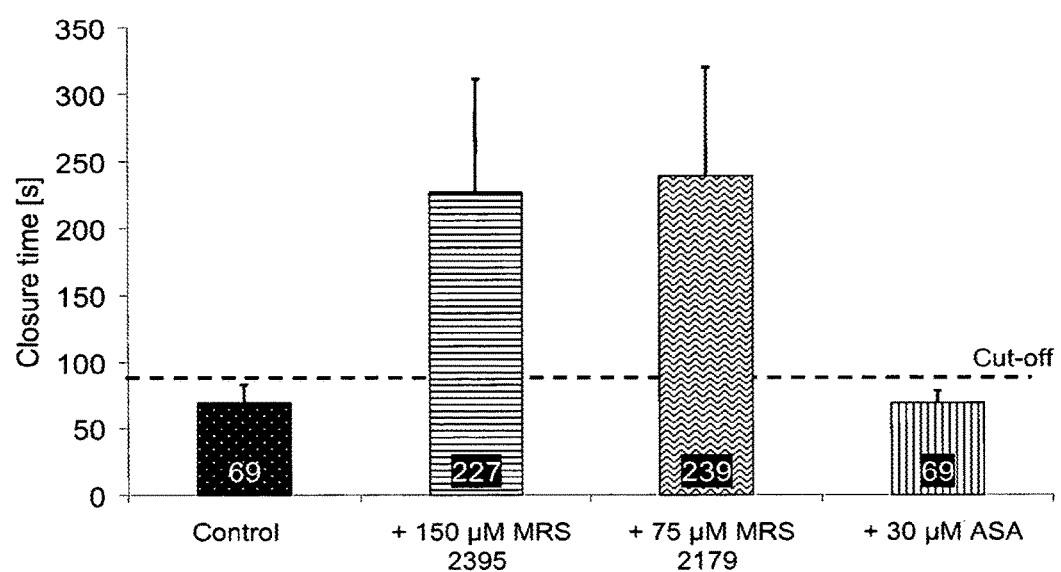

The results of the investigations are summarized in FIG. 3 and the relevant figure description.

In Table 3 details are given for how many of the respective 10 MRS 2395-, MRS 2179- or acetylsalicylic acid-treated samples a closure time above the cut-off was measured with the aid of the ADP/PGE1 test cartridge according to the invention. In 9 of the 10 samples treated with MRS 2395 and in 10 of the 10 samples treated with MRS 2179 an abnormally reduced platelet aggregation was measured with the aid of the method of the invention, whereas none of the samples treated with acetylsalicylic acid was classified as abnormal. This means that the method according to the invention has a high sensitivity for a platelet dysfunction induced both by a P2Y(12) antagonist and by a P2Y(1) antagonist. Moreover, it is of advantage that the method according to the invention has a very low sensitivity for acetylsalicylic acid in the presence of free calcium ions.

Thus on the basis of its high sensitivity for platelet dysfunction induced by ADP receptor antagonists and its low sensitivity towards platelet dysfunction induced by acetylsalicylic acid the method according to the invention is suitable for differentiation of the two classes of antithrombotics.

TABLE 3

| | Number of samples with closure times above cut-off (n = 10) Sample | | |
|---|---|---|---|
| Test cartridge | MRS 2395 (P2Y(12) antagonist) | Acetylsalicylic acid (COX-1 inhibitor) | MRS 2179 (P2Y(1) antagonist) |
| ADP/PGE1 | 9 | 0 | 10 |

4c) Determination of the Cut-Off for ADP/PGE Test Cartridges

Owing to the use of PPACK as anticoagulant the cut-off determined with citrated whole blood in the above-described examples cannot be used. Therefore, the reference range for the ADP/PGE1 closure time from the 10 samples of the healthy donors treated with PPACK was calculated by the determination of the 90% central interval of the normal distribution of the mean values of the duplicate determinations. This gave the following reference ranges for the closure times:

ADP/PGE1 51-90 seconds.

The upper limit of the 90% central interval was defined as cut-off, i.e. as threshold value for a platelet dysfunction.

The invention claimed is:

1. A method for the determination of an antithrombotic effect of a P2Y(12) antagonist or a P2Y(1) antagonist in a whole blood sample, the method comprising the following steps:
    a) passing the blood through a capillary and then through an opening of a partition member; and
    b) measuring the time that is required for the formation of a thrombus at the opening of the partition member up to closure of the opening;
    wherein the partition member comprises:
        i) an activator of purinergic receptors;
        ii) an activator of intracellular adenylate cyclases; and
        iii) calcium ions;
    wherein the whole blood sample comprises one or more of the P2Y(12) antagonist and the P2Y(1) antagonist, and optionally an acetylsalicylic acid, and
    wherein the time measured in step (b) indicates the antithrombotic effect of the P2Y(12) antagonist or the P2Y(1) antagonist in the whole blood sample, and wherein the time measured in step (b) does not indicate the antithrombotic effect of the acetylsalicylic acid in the whole blood sample.

2. The method of claim 1, wherein the partition member used comprises an activator of purinergic receptors from the group adenosine-5'-diphosphate, 2-methylthioadenosine-5'-diphosphate, and their derivatives.

3. The method of claim 1, wherein the partition member comprises an activator of intracellular adenylate cyclases from the group prostaglandin E1, forskolin and their derivatives, prostaglandin I2 and its stable derivatives, illoprost, and cicaprost.

4. The method of claim 1, wherein the whole blood sample is anticoagulated with a direct thrombin inhibitor.

5. The method of claim 1, wherein the whole blood sample is anticoagulated with a direct Factor Xa inhibitor.

6. The method of claim 1, wherein the whole blood sample is anticoagulated with citrate.

7. The method of claim 1, wherein the P2Y(12) antagonist is selected from clopidogrel, ticlopidine, prasugrel, AR-C67085MX, cangrelor, C1330-7, MRS 2395, and 2-methylthioadenosine-5'-monophosphate.

8. The method of claim 1, wherein the P2Y(1) antagonist is selected from MRS 2179, MRS 2279, MRS 2500, A2P5P, A3P5P, and A3P5PS.

9. The method of claim 3, wherein the activator of intracellular adenylate cyclases is prostaglandin E1.

* * * * *